United States Patent
Slater et al.

(10) Patent No.: US 11,874,230 B2
(45) Date of Patent: Jan. 16, 2024

(54) AUGMENTED RAMAN ANALYSIS USING ABSOLUTE RAMAN

(71) Applicant: Endress+Hauser Optical Analysis, Inc., Ann Arbor, MI (US)

(72) Inventors: Joseph B. Slater, Dexter, MI (US); Marc Winter, Gelnhausen (DE); Oliver Link, Gundelfingen (DE)

(73) Assignee: Endress+Hauser Optical Analysis, Inc., Ann Arbor, MI (US)

( * ) Notice: Subject to any disclaimer, the term of this patent is extended or adjusted under 35 U.S.C. 154(b) by 0 days.

(21) Appl. No.: 17/806,134

(22) Filed: Jun. 9, 2022

(65) Prior Publication Data

US 2023/0400413 A1 Dec. 14, 2023

(51) Int. Cl.
*G01N 21/65* (2006.01)
*G01N 9/24* (2006.01)
*G01N 33/00* (2006.01)

(52) U.S. Cl.
CPC ............... *G01N 21/65* (2013.01); *G01N 9/24* (2013.01); *G01N 33/0027* (2013.01)

(58) Field of Classification Search
CPC ...... G01N 21/65; G01N 33/0027; G01N 9/24; G01J 3/44; G01K 13/00; G01K 13/024; G01L 23/00
See application file for complete search history.

(56) References Cited

U.S. PATENT DOCUMENTS

| | | | | |
|---|---|---|---|---|
| 5,341,206 A | * | 8/1994 | Pittaro | G01N 21/65 250/252.1 |
| 6,634,214 B1 | * | 10/2003 | Thurston | G05D 21/02 73/32 A |
| 10,768,115 B2 | | 9/2020 | Slater et al. | |
| 10,921,184 B2 | * | 2/2021 | Alon | H01S 5/4087 |
| 2019/0256359 A1 | * | 8/2019 | Hennet | C01B 32/205 |

* cited by examiner

*Primary Examiner* — Tarifur R Chowdhury
*Assistant Examiner* — Kemaya Nguyen
(74) *Attorney, Agent, or Firm* — Mark A. Logan; Endress+Hauser (USA) Holding, Inc.

(57) ABSTRACT

A method for determining an amount of a Raman-invisible gas in a multi-component gas stream includes performing a first and second absolute Raman analysis on the gas stream. A decrease in the absolute Raman bands from the first analysis to the second analysis is attributed to an increase of the Raman-invisible gas in the gas stream. The amount of the Raman-invisible gas is calculated from the difference between the first and second sets of Raman bands. The calculation of the Raman-invisible gas is verified via a measurement and a calculation of a secondary property of the gas stream such as the thermal conductivity of the gas stream or the density of the gas stream.

6 Claims, 1 Drawing Sheet

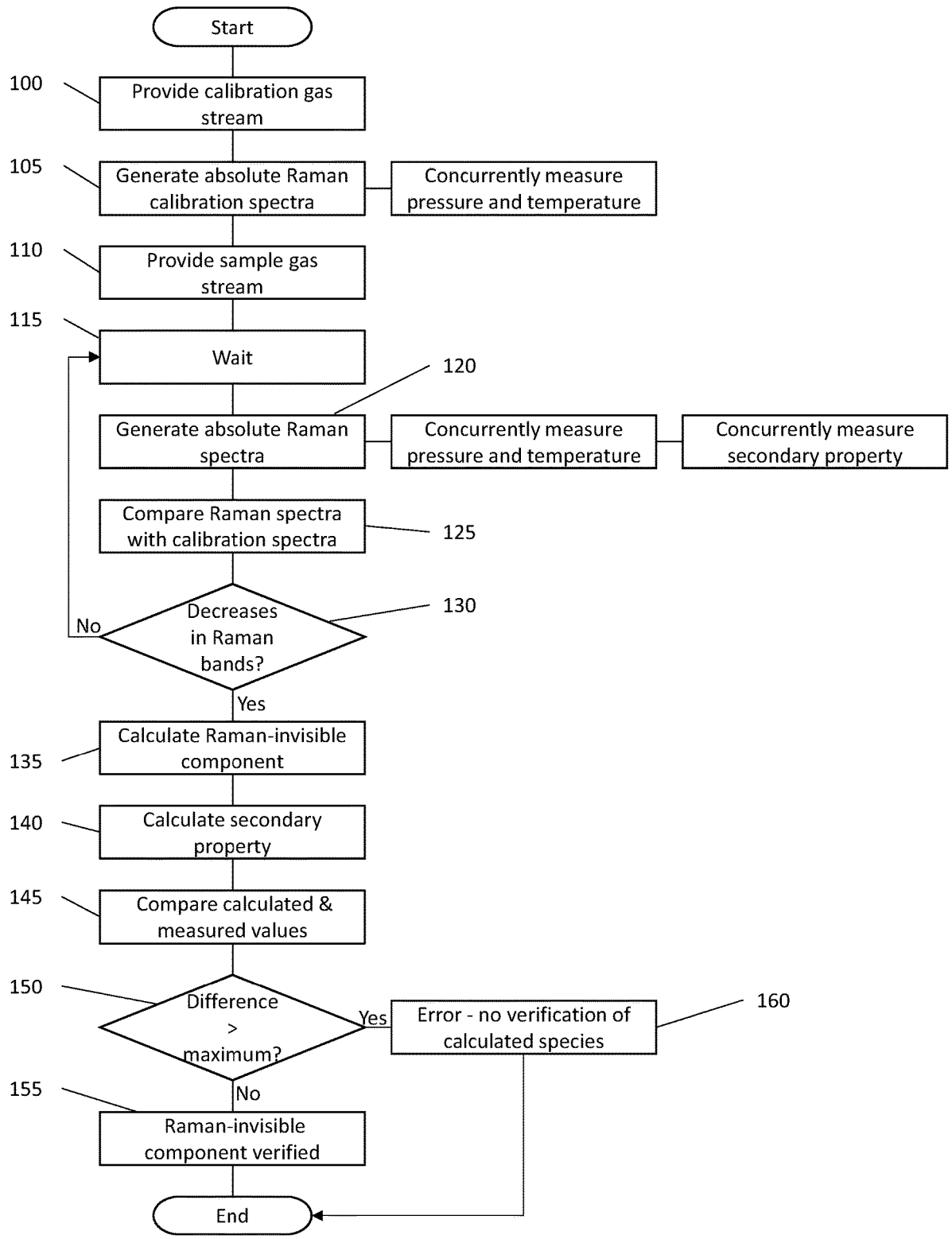

AUGMENTED RAMAN ANALYSIS USING ABSOLUTE RAMAN

TECHNICAL FIELD

The present disclosure relates generally to a method of using Raman spectroscopy and a secondary measurement to determine an amount of Raman-invisible gas in a gas sample.

BACKGROUND OF THE INVENTION

Composition analysis of a gas sample by Raman spectroscopy allows the measurement of the abundance of the chemical species within the gas sample for those chemical species composed of at least two atoms. Species composed of just one atom, such as the noble gases helium and argon, and ionic-bonded substances like salts, are invisible to Raman spectroscopy. In practice, such Raman-invisible species are present in some chemical mixtures and often need to be quantified.

In sample streams containing a component invisible to Raman spectroscopy, it is often necessary to supplement the spectroscopy measurements to quantify invisible species and obtain full composition analysis. For example, in the synthesis loop in a fertilizer plant argon is present along with other gases. Though Raman spectroscopy can characterize most of the gases in a sample, the detection of argon requires another technology such as gas chromatography or mass spectrometry. These methods are relatively expensive and not well suited to in situ detection within a pipeline or a reactor.

Often in a Raman spectroscopic analysis of a gas sample the Raman bands are normalized so that each component of the gas sample is expressed as a ratio to the whole. Such normalization of the bands makes the Raman analysis insensitive to small changes in laser output. However, expressing each component as a ratio to the whole is not a complete analysis when there is a Raman-unseen component within the gas stream sample: the whole is not known, and indeed that is what is sought.

A Raman spectroscopic analysis of a sample gas stream may also use absolute Raman spectral bands to determine the amounts of Raman-visible gases in the sample gas stream. In absolute Raman analysis, the amounts of the Raman-visible gases are determined directly from the Raman spectral bands. Although absolute Raman analysis obviates the problem of expressing components as a ratio to an unknown whole, absolute Raman analysis is sensitive to small changes in laser output or to any other system variability that would cause an increase or decrease in absolute signal level. For example, a kink in the fiber optic line that carries the light from the laser to the gas sample may reduce the amount of light exposing the gas sample. Or a kink in the fiber optic line that carries light (i.e., the Raman signal) from the sample to the analyzer may reduce the amount of light detected from the gas sample. Any reduction in the output of the laser or in the return signal—such reductions being caused by any number of things—will result in reduced absolute Raman bands. In practice it is difficult to detect the cause for the reduced absolute Raman bands: a lower amount of the constituents of the gas sample will also show as reduced absolute Raman bands.

Whether using normalized Raman bands or absolute Raman bands, the problem of using Raman spectroscopy to find Raman-invisible components in a gas stream remains. Accordingly, there remains a need for further contributions in this area of technology to enable compositional analysis of mixtures that include spectroscopic-invisible species.

SUMMARY OF THE INVENTION

According to at least one embodiment of the disclosure, a method for determining an amount of a Raman-invisible gas in a sample gas stream may comprise providing a Raman spectroscopic device, including a Raman laser performing a Raman analysis of a calibration gas stream, wherein the Raman analysis of the calibration gas stream includes measuring a pressure and a temperature of the calibration gas stream; determining a first set of absolute Raman bands from the Raman analysis of the calibration gas stream, wherein the first set of absolute Raman bands correlate to Raman-visible gases within the calibration gas steam; calculating, using the first set of absolute Raman bands, first amounts of each Raman-visible gas present in the calibration gas stream; waiting a first time period; performing a Raman analysis of the sample gas stream, wherein the Raman analysis of the sample gas stream includes measuring a pressure and a temperature of the sample gas stream; determining a second set of absolute Raman bands from the Raman analysis of the sample gas stream, wherein the second set of absolute Raman bands correlate to the Raman-visible gases within the sample gas stream; calculating, using the second set of absolute Raman bands, second amounts of each Raman-visible gas present in the sample gas stream; comparing the amount of each Raman-visible gas in the sample gas stream to the respective amount of each Raman-visible gas in the calibration gas stream; attributing decreases in the amounts of the Raman-visible gases in the sample gas stream to a displacement of the Raman-visible gases in the sample gas stream by a Raman-invisible gas in the sample gas stream; and calculating the amount of the Raman-invisible gas in the sample gas stream using the decreases in the amounts of the Raman-visible gases in the sample gas stream.

An embodiment of the method may further comprise measuring a first power of the Raman laser during the Raman analysis of the calibration gas stream; measuring a second power of the Raman laser during the Raman analysis of the sample gas stream; and adjusting the second set of absolute Raman bands to compensate for a difference between the first power of the Raman laser and the second power of the Raman laser.

An embodiment of the method may further comprise measuring a first value of a secondary property of the sample gas stream during the Raman analysis of the sample gas stream; calculating a second value of the secondary property of the sample gas stream using: the second amounts of each Raman-visible gas; the amount of the Raman-invisible gas; and reference values for the secondary property of each respective Raman-visible gas and of the Raman-invisible gas; comparing the measured first value of the secondary property with the calculated second value of the secondary property; when a difference between the measured value of the secondary property and the calculated value of the secondary property is less than or equal to a difference threshold, indicate the calculated amount of the Raman-invisible gas as verified; and when the difference between the measured value of the secondary property and the calculated value of the secondary property is greater than the difference threshold, indicate the calculated amount of the Raman-invisible gas as unverified.

An embodiment of the method may further comprise adjusting the contents of the calibration gas stream based on the second amounts of the Raman-visible components; and repeating the method steps recited in claim 1 beginning with performing a Raman analysis of the calibration gas stream.

In an embodiment of the disclosed method, the Raman-invisible gas may be Argon, and when the secondary property may be a density of the gas sample.

In an embodiment of the disclosed method, the Raman-invisible gas may be Argon, and wherein the secondary property may be a thermal conductivity of the gas sample.

BRIEF DESCRIPTION OF THE DRAWINGS

FIG. 1 shows a flowchart of the method according to an embodiment of the present disclosure.

DETAILED DESCRIPTION

Disclosed herein is a method for determining an amount of a Raman-invisible component of a multi-component gas stream using Raman spectroscopy and a measured property of the gas stream. The disclosed method measures decreases in the absolute Raman bands measured in Raman spectrographs over time and attributes the decreases in the absolute Raman bands to a displacement of the Raman-visible gases in the gas stream by a Raman-invisible gas that is increasing in the gas stream. The amount of the Raman-invisible gas is deduced and calculated from the decreases in the absolute Raman bands. A secondary property of the gas stream is measured to verify the calculations made from the Raman analyses. Various embodiments of the disclosed method will now be presented in conjunction with the figures that illustrate the embodiments. It will be understood that no limitation of the scope of this disclosure is thereby intended.

FIG. 1 shows a flowchart according to an embodiment of the present disclosure. In a first step 100 of the disclosed method, a calibration gas stream may be provided for the calibration of the Raman spectroscopic equipment. The calibration gas stream may be a multi-component gas the does not include any Raman-invisible component.

In this context, multi signifies one or more gases may be present. That is, in this and the following context, multi signifies at least one.

In a step 105 of the disclosed method, an absolute Raman analysis may be made of the calibration gas stream. The Raman calibration spectra generated in the Raman analysis of the calibration gas stream may provide a baseline against which subsequent Raman spectra may be compared. The baseline may provide a picture of the Raman spectra when no Raman-invisible component is present, and thus decreases of the Raman bands over time—when compared with the calibration spectra—may be used to infer and to calculate a presence of a Raman-invisible gas that is displacing the Raman-visible gases from the gas stream.

During the Raman analysis of the calibration gas stream, the power of the laser exposing the calibration gas stream may be determined. The laser power may be determined by monitoring the control program of the laser or by separately measuring the laser power within the gas stream. The laser power as determined during the Raman analysis of the calibration gas stream may be compared with the laser power measured during subsequent Raman analyses to help determine if any changes in the Raman bands should be attributed to changes in the laser's power.

Concurrently with the step 105 in which the Raman calibration spectra are generated, a pressure and a temperature of the gas steam (in this case, of the calibration gas stream) are also measured. In this context, concurrent means near enough in time to measure the conditions within the container or vessel that prevailed during the Raman measurement. The values for the pressure and the temperature are used along with the absolute Raman spectra to determine and to calculate the amounts of the various components of the calibration gas stream. Such calculations using the absolute Raman spectra, the pressure, and the temperature to determine the components of a gas sample are well known in the art.

In a next step 110 of the disclosed method, a multi-component sample gas stream is provided. The multi-component sample gas stream may include an amount of a gas that is invisible to Raman spectroscopy. The sample gas stream may be contained in a shift converter within an ammonia processing plant, for example, but this is not a requirement. The sample gas stream may be contained in any container or vessel where Raman measurements and pressure and temperature measurements may be made.

In a next step 115 of the disclosed method, a process within the shift converter, container, or vessel may be allowed to run. For example, an ammonia synthesis may be allowed to continue within the shift converter of the ammonia processing plant. However, the disclosed method is not limited to an ammonia synthesis process, but is applicable to any process using or producing a gas within a container or vessel.

In a next step 120 of the disclosed method, an absolute Raman analysis may be made of the sample gas stream. As with the absolute Raman analysis of the calibration gas stream, the absolute Raman analysis of the sample gas stream may generate a series of Raman bands that indicate the types and amounts of the Raman-visible gas components in the sample gas stream.

During the Raman analysis of the sample gas stream, the power of the laser exposing the calibration gas stream may be determined. The laser power measured during the analysis of the sample gas stream may then be compared with the laser power measured during the analysis of the calibration gas stream, and the bands from the Raman analysis of the sample gas stream may be then adjusted for any increases or decreases in the measured laser power.

Concurrently with the Raman analysis of the sample gas stream, a pressure of the sample gas stream and a temperature of the sample gas stream may both be measured. From the absolute Raman spectra of the sample gas stream, the measured pressure, and the measured temperature, the amounts of the various Raman-visible components of the sample gas stream are determined and calculated.

In addition to measuring the pressure and the temperature of the sample gas stream, also concurrently with the step 120 of performing the Raman analysis of the sample gas stream a secondary property of the sample gas stream may be measured. The secondary property of the sample gas stream may be any physical property of the sample gas stream that depends upon the constituents of the sample gas stream and therefore changes in value as the constituents of the sample gas stream change. For example, the secondary property may be the density of the sample gas stream, and this (i.e., the density value) may change if a heavier, or a lighter, gas is added to the sample gas stream. Alternately, as a further example, the secondary property may be the thermal conductivity of the gas stream.

In a next step 125 of the disclosed method, the bands of the absolute Raman analysis of the sample gas stream are compared with the bands of the absolute Raman analysis of the calibration gas stream to determine if there were decreases in the respective amounts of the Raman-visible components as shown in the Raman spectra. A decrease in only one or two Raman-visible components of a multi-component sample gas stream (i.e., a decrease from the Raman spectra of the calibration gas stream to the Raman spectra of the sample gas stream) may be due to a process or reaction within the shift converter, container, or vessel, and may not be due to displacement of those one or two components by a Raman-invisible gas. Rather, the disclosed method looks for decreases in the Raman bands of several components of the sample gas stream to attribute such decreases to a displacement of those component gases by a Raman-invisible gas. This checking for decreases in the absolute Raman bands is step 130 of the method as flowcharted in FIG. 1.

When no decreases in the Raman bands are detected, the method returns to the step 115 of allowing the process within the shifter converter, container, or vessel to run.

In a step 135 of the disclosed method, once it has been determined that the Raman bands show decreases in the amounts of the Raman-visible gases in the sample gas stream, an amount of a Raman-invisible component is calculated. The calculation of the Raman-invisible component uses as inputs the differences between the Raman spectra from the calibration gas stream and the Raman spectra of the sample gas stream.

Although at this point in the method the amount of the Raman-invisible gas is now known, having been calculated from the differences in the Raman spectra, the calculated amount of the Raman-invisible gas will be verified using the measured secondary property of the gas stream.

In a step 140 of the disclosed method, a value of the secondary property of the sample gas stream—the same secondary property that was measured concurrently with the Raman analysis of the sample gas stream—may be calculated. The value of the secondary property may be calculated using the amounts of the Raman-visible gases determined from the Raman analysis of the sample gas stream including the calculated amount of the Raman-invisible gas. In this step 140 of the disclosed method, it is necessary to make an assumption of the particular species that makes up the Raman-invisible gas so that the particular secondary property may be correctly calculated. For example, in the previous example of a shift converter in an ammonia processing plant, it may be assumed that the Raman-invisible gas is argon.

As a first example of the calculation of the secondary property, the density of the gas stream is calculated from: the amounts of each Raman-visible component determined from the Raman analysis of the sample gas stream; density values for each of the Raman-visible components as determined from reference literature; the calculated amount of the Raman-invisible gas; the density value (as taken from reference literature) of the Raman-invisible gas; and the pressure and temperature measured at the Raman analysis of the sample gas stream. As a second example of the calculation of the secondary property, the thermal conductivity of the gas stream may be calculated in an analogous way, using the determined amounts of the various Raman visible gases, the calculated amount of the Raman-invisible gas, values for thermal conductivity for these gases as taken from reference literature, and the pressure and temperature measured during the Raman analysis of the sample gas stream.

Many different secondary properties of the gas stream may be used analogously to these examples of density and thermal conductivity. What is necessary is that the selected secondary property be dependent upon the particular kinds and amounts of gas species present in the sample gas stream and that the selected secondary property of the Raman-invisible species be different from the secondary property of the other gases in the sample gas stream. That is, an increasing amount of the Raman-invisible gas must raise (or lower) the value of the selected secondary property (from the value of that secondary property when the Raman-invisible gas is not present) so that the Raman-invisible gas's contribution to the value of the secondary property may be calculated.

In a step 145 of the disclosed method, the measured and calculated values of the secondary property are compared. Regardless if there is a Raman-invisible gas in the sample gas stream, these two values (i.e., the measured and the calculated) should differ by less than a predetermined maximum difference. However, when there is a Raman-invisible gas within the sample gas stream, and when the measured and calculated values of the secondary property differ by no more than the predetermined maximum difference, then the amount of the Raman-invisible gas was correctly calculated. Or stated in another way, because the calculated value of the secondary property was calculated using the calculated amount of the Raman-invisible gas, and because the calculated value of the secondary property differs from the measured value of the secondary property by no more than the predetermined maximum difference, then the calculated amount of the Raman-invisible gas must be correct. This is shown in step 155 of FIG. 1.

Of course, when the calculated value of the secondary property of the sample gas stream differs from the measured value of the secondary property by more than the predetermined maximum difference, then the calculated value of the Raman-invisible gas may not be correct. In this case, the system should raise a warning or error or alarm to indicate the calculated value of the Raman-invisible gas may not be correct. This is shown in step 160 of FIG. 1.

The disclosed method may be repeated, or run in a loop, during the process in which the Raman-invisible gas is produced. If the calculated amount of the Raman-invisible gas (as calculated in step 135) is verified in step 155, then the method may be repeated from the step 115 of letting process in the shift converter, container, or vessel run. However, if the calculated amount of the Raman-invisible gas was not verified in step 155, then the method may be repeated from the beginning (i.e., step 100) by providing a calibration gas stream. In this case, it may be helpful to more closely match the calibration gas stream with the Raman-visible components as determined by the Raman analysis of the sample gas stream.

What is claimed:

1. A method for determining an amount of a Raman-invisible gas in a sample gas stream, the method comprising:
   providing a Raman spectroscopic device, including a Raman laser;
   performing a Raman analysis of a calibration gas stream, wherein the Raman analysis of the calibration gas stream includes measuring a pressure and a temperature of the calibration gas stream;
   determining a first set of absolute Raman bands from the Raman analysis of the calibration gas stream, wherein the first set of absolute Raman bands correlate to Raman-visible gases within the calibration gas stream;
   calculating, using the first set of absolute Raman bands, first amounts of each Raman-visible gas present in the calibration gas stream;
   waiting a first time period;

performing a Raman analysis of the sample gas stream, wherein the Raman analysis of the sample gas stream includes measuring a pressure and a temperature of the sample gas stream;

determining a second set of absolute Raman bands from the Raman analysis of the sample gas stream, wherein the second set of absolute Raman bands correlate to the Raman-visible gases within the sample gas stream;

calculating, using the second set of absolute Raman bands, second amounts of each Raman-visible gas present in the sample gas stream;

comparing the amount of each Raman-visible gas in the sample gas stream to the respective amount of each Raman-visible gas in the calibration gas stream;

attributing decreases in the amounts of the Raman-visible gases in the sample gas stream to a displacement of the Raman-visible gases in the sample gas stream by the Raman-invisible gas in the sample gas stream; and calculating the amount of the Raman-invisible gas in the sample gas stream using the decreases in the amounts of the Raman-visible gases in the sample gas stream.

2. The method according to claim 1, further comprising:
measuring a first power of the Raman laser during the Raman analysis of the calibration gas stream;
measuring a second power of the Raman laser during the Raman analysis of the sample gas stream; and
adjusting the second set of absolute Raman bands to compensate for a difference between the first power of the Raman laser and the second power of the Raman laser.

3. The method according to claim 1, further comprising:
measuring a first value of a secondary property of the sample gas stream during the Raman analysis of the sample gas stream;

calculating a second value of the secondary property of the sample gas stream using: the second amounts of each Raman-visible gas; the amount of the Raman-invisible gas; and reference values for the secondary property of each respective Raman-visible gas and of the Raman-invisible gas;

comparing the measured first value of the secondary property with the calculated second value of the secondary property;

when a difference between the measured value of the secondary property and the calculated value of the secondary property is less than or equal to a difference threshold, indicate the calculated amount of the Raman-invisible gas as verified; and when the difference between the measured value of the secondary property and the calculated value of the secondary property is greater than the difference threshold, indicate the calculated amount of the Raman-invisible gas as unverified.

4. The method according to claim 3, further comprising:
adjusting the contents of the calibration gas stream based on the second amounts of the Raman-visible components; and
repeating the method steps recited in claim 1 beginning with performing a Raman analysis of the calibration gas stream.

5. The method of claim 3,
wherein the Raman-invisible gas is Argon, and
wherein when the secondary property is a density of the gas sample.

6. The method of claim 3,
wherein the Raman-invisible gas is Argon, and
wherein the secondary property is a thermal conductivity of the gas sample.

* * * * *